(12) United States Patent
Fan et al.

(10) Patent No.: US 8,992,426 B2
(45) Date of Patent: *Mar. 31, 2015

(54) FEEDBACK IN MEDICAL ULTRASOUND IMAGING FOR HIGH INTENSITY FOCUSED ULTRASOUND

(75) Inventors: Liexiang Fan, Sammamish, WA (US); Kevin Sekins, Yallow Point, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1022 days.

This patent is subject to a terminal disclaimer.

(21) Appl. No.: 12/869,280

(22) Filed: Aug. 26, 2010

(65) Prior Publication Data
US 2010/0317971 A1  Dec. 16, 2010

Related U.S. Application Data

(63) Continuation-in-part of application No. 12/435,196, filed on May 4, 2009, now Pat. No. 8,343,050.

(51) Int. Cl.
| A61B 8/00 | (2006.01) |
| A61N 7/02 | (2006.01) |
| A61B 8/08 | (2006.01) |
| G01S 7/52 | (2006.01) |
| G01S 15/89 | (2006.01) |
| A61B 19/00 | (2006.01) |

(52) U.S. Cl.
CPC ... *A61N 7/02* (2013.01); *A61B 8/08* (2013.01); *A61B 8/485* (2013.01); *G01S 7/52036* (2013.01); *G01S 7/52042* (2013.01); *G01S 15/899* (2013.01); *G01S 15/8993* (2013.01); *A61B 19/56* (2013.01); *A61B 2019/5276* (2013.01)
USPC ............ 600/437; 600/407; 600/441; 600/443

(58) Field of Classification Search
USPC .................. 600/437, 441, 407, 443
See application file for complete search history.

(56) References Cited

U.S. PATENT DOCUMENTS

| 5,107,837 A | 4/1992 | Ophir et al. |
| 5,178,147 A | 1/1993 | Ophir et al. |
| 5,293,870 A | 3/1994 | Ophir et al. |
| 5,810,731 A | 9/1998 | Sarvazyan et al. |
| 6,508,768 B1 | 1/2003 | Hall et al. |
| 6,558,324 B1 | 5/2003 | Von Behren et al. |
| 6,764,448 B2 | 7/2004 | Nightingale et al. |
| 6,770,033 B1 | 8/2004 | Fink et al. |
| 6,951,544 B2 | 10/2005 | Trahey et al. |
| 8,343,050 B2 * | 1/2013 | Fan et al. ............... 600/437 |
| 2005/0252295 A1 | 11/2005 | Fink et al. |
| 2008/0097206 A1 | 4/2008 | Chomas et al. |
| 2008/0125657 A1 | 5/2008 | Chomas et al. |
| 2009/0216119 A1 | 8/2009 | Fan et al. |

OTHER PUBLICATIONS

U.S. Appl. No. 12/435,196, filed May 4, 2009.

* cited by examiner

*Primary Examiner* — Joel Lamprecht

(57) ABSTRACT

Feedback of position is provided for high intensity focused ultrasound. The location of a beam from a HIFU transducer is determined using ultrasound imaging. The ultrasound imaging detects tissue displacement caused by a beam transmitted from the HIFU transducer. The displacement or information derived from the displacement may be used to determine a center line or point location (e.g., foci) of the tissues response to HIFU. The location of the line or point may be displayed in an image, such as an overlay or by color coding.

21 Claims, 3 Drawing Sheets

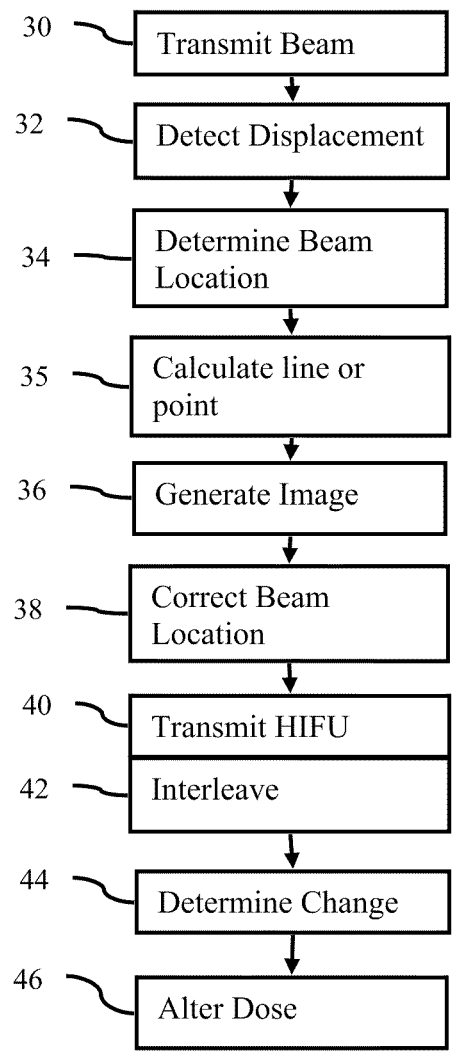
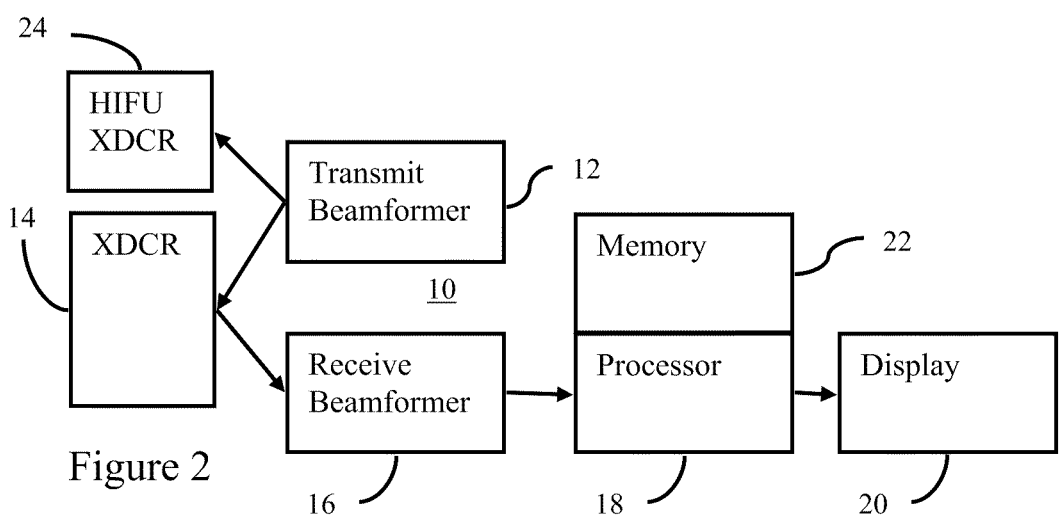

FEEDBACK IN MEDICAL ULTRASOUND IMAGING FOR HIGH INTENSITY FOCUSED ULTRASOUND

RELATED APPLICATIONS

The present patent document is a continuation-in-part of application Ser. No. 12/435,196 filed May 4, 2009, which is hereby incorporated by reference.

FEDERALLY SPONSORED RESEARCH OR DEVELOPMENT

The U.S. Government has a paid-up license in this invention and the right in limited circumstances to require the patent owner to license others on reasonable terms as provided by the terms of contract no. HR 0011-08-3-0004 awarded by DARPA.

BACKGROUND

The present embodiments relate to ultrasound imaging. In particular, ultrasound imaging is used for feedback in high intensity focused ultrasound (HIFU).

HIFU is used to treat cancers, tumors, lesions, or other undesired tissue structures. Ultrasound energy heats the tissue sufficiently to necrotize the undesired tissue. The ultrasound energy is focused to avoid harming healthy tissue. Treatment with ultrasound may avoid invasive procedures, such as an operation or radio frequency ablation procedure.

Ultrasound imaging has been used to guide HIFU therapy. The imaging assists in focusing the therapy pulses on the undesired tissue. For example, a same array is used to image and transmit HIFU so that the HIFU is focused at the desired tissue. However, the HIFU may use a different array than used for imaging. Also, gas bubbles or cavitation during application of HIFU may result in inaccurate identification of the HIFU treatment region.

Attempts have also been made to monitor the thermal and biological changes of the tissue during these therapies. For example, ultrasound energy is used to measure thermal expansion coefficients (e.g., measure tissue expansion by speckle tracking), speed of sound in the tissue, or stiffness changes (e.g., strain imaging). However, these diagnostic based ultrasound tissue characterizations may not have sufficient signal-to-noise resolution or may not be clinically viable.

BRIEF SUMMARY

By way of introduction, the preferred embodiments described below include methods, instructions, and systems for providing feedback for high intensity focused ultrasound. The location of a beam from a HIFU transducer is determined using ultrasound imaging. The ultrasound imaging detects tissue displacement caused by a beam transmitted from the HIFU transducer. The displacement or information derived from the displacement may be used to determine a center line, point location (e.g., foci), or other shape of the tissue's response to HIFU. The location of the line, shape, or point may be displayed in an image, such as an overlay or by color coding.

In a first aspect, a computer readable storage medium has stored therein data representing instructions executable by a programmed processor for providing feedback for high intensity focused ultrasound. The storage medium includes instructions for transmitting an emulation of a high intensity focused ultrasound therapy waveform, the emulation having a different amplitude, duration, or both amplitude and duration from the therapy waveform, the emulation substantially avoiding therapy heating and cavitation, determining displacements at a plurality of locations in a multi-dimensional region with ultrasound scanning, the locations of displacements being caused by the emulation, computing a shape of the displacements, and generating an image highlighting the shape.

In a second aspect, a method is provided for feedback about high intensity focused ultrasound. An excitation is transmitted from a high intensity focused ultrasound transducer into tissue of a patient. Displacements of the tissue caused by the excitation are detected. A shape for a response of the tissue to the excitation is calculated as a function of the displacements of the tissue. An image indicates the shape relative to the tissue.

In a third aspect, a system provides for feedback for high intensity focused ultrasound. A receive beamformer is operable to output data representing spatial locations as a function of received acoustic signals. A processor is operable to estimate tissue displacements as a function of the output data, determine a sub-region of a region of contiguous tissue displacements, and generate an image with the sub-region highlighted. A display is operable to display the image of the sub-region.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a flow chart diagram of one embodiment of a method for providing feedback for high intensity focused ultrasound;

FIG. 2 is a block diagram of one embodiment of a system for providing feedback for high intensity focused ultrasound;

DETAILED DESCRIPTION OF THE DRAWINGS AND PRESENTLY PREFERRED EMBODIMENTS

Figure 3:
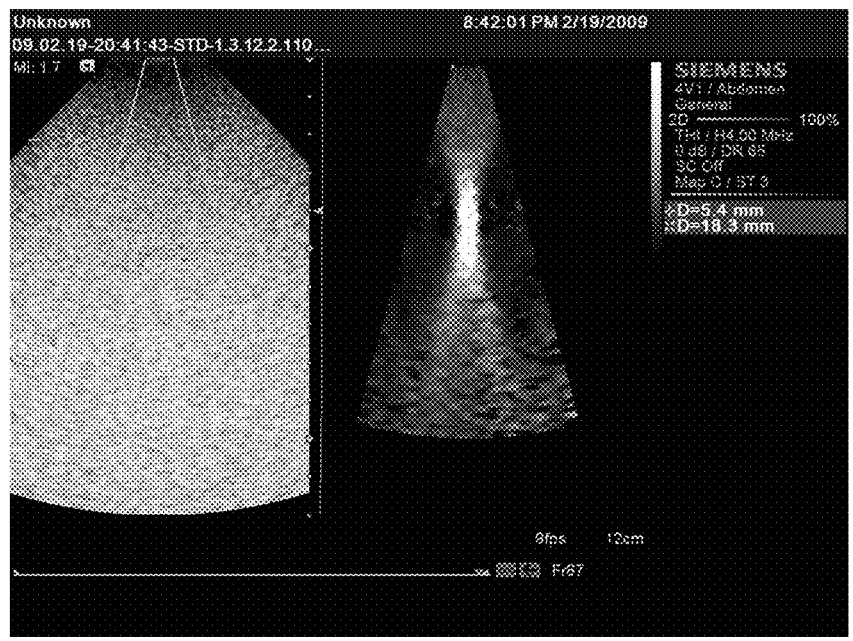
FIG. 3 is a medical image showing a tissue region and a detected beam profile.

Detecting the therapy beam or an emulation of the beam from displacement may account for phase aberrations and/or attenuation. Dose distribution may be better estimated using displacement imaging, such as elasticity, strain, or shear. The results of displacement imaging may be used to correct distribution of the therapy beam. The therapy transducer power and/or focus location may be adjusted based on the feedback. The HIFU transducer may be adjusted, such as aimed, based on the feedback.

Effects caused by bubbles or cavitation at different depths from the focal location may affect the treatment result. By identifying the center line, shape (e.g., arrow representing the center line, curve representing beam edges, ellipse representing general beam area or volume), or a point location within the beam distribution, the HIFU focus or scan line may be adjusted or reconfigured to correct for any undesired dose distribution. The therapy plan may be altered to account for pre- or post-focal depth effects or events. HIFU application may be monitored to determine shifts in the focal location, beam shape, and/or center line.

In one example use, a region of a patient is scanned with ultrasound. A HIFU transducer is used to deliver a testing or HIFU excitation to a target to be treated in the region. The region is scanned again with ultrasound. The tissue's response to the excitation, including displacement or a measurement derived from displacement (e.g., shear or strain), is computed. A center line or point of the tissues response in the multi-dimensional region is computed. The computation may be interleaved with the HIFU treatment, allowing monitoring and redirecting the HIFU beam as desired during the treatment. The computation of the point may detect multiple points due to tissue response, indicating multiple locations likely to be associated with cavitation or bubble generation.

FIG. 1 shows a method for providing feedback for high intensity focused ultrasound. The method is implemented by the system of FIG. 2 or a different system. Additional, different, or fewer acts may be provided. For example, acts 38-46 are not provided in some embodiments. The acts are performed in the order described or shown, but may be performed in other orders. For example, the beam location is corrected in act 38 prior to generating the image in act 36. As another example, acts 32-36 are repeated with act 40 as part of the interleaving of act 42. One or more transmissions for act 32 may occur prior to act 30.

In act 30, an excitation is transmitted from a high intensity focused ultrasound transducer. The excitation is acoustic energy. The acoustic energy is focused, resulting in a three-dimensional beam profile. The excitation is focused using a phased array and/or mechanical focus. The excitation may be unfocused in one dimension, such as the elevation dimension. The excitation is transmitted into tissue of a patient. The excitation is focused at a location for treatment, such as a tumor. However, due to acoustic effects, misalignment, or other factors, the beam may not properly overlap, cover, or even intersect the tissue location for treatment.

The excitation is generated as therapy excitation. Alternatively, the excitation emulates the therapy excitation. The high intensity focused ultrasound therapy waveform is emulated. A generally same focus, amplitude, frequency, or other characteristic as the therapy excitation is provided for the emulation. The emulation is used to substantially avoid therapeutic effect. For example, the amplitude, duration, or both are reduced as compared to a therapy waveform (e.g., Isppa on the order of about 200 W/cm$^2$ and duration on the order of about 600 micro seconds). "Substantially" avoiding therapeutic effect allows for generalization to a region, such as the region of treatment. A single point may be heated above a threshold level due to aberrations or focal distortion, but the treatment region overall avoids therapeutic effect from the emulation. Avoiding therapeutic effect may be avoiding heating to the point of altering the tissue or creating cavitations. For example, biological effects may include hyperthermia at tissue temperature of about 41-45° C., protein denaturation at temperatures above 45° C., and tissue necrosis at temperatures above 50° C. Tissue stiffness may be affected even at temperatures below 45° C. At temperatures above 45° C., increases in viscosity and/or stiffness may occur. At temperatures above 50° C., the tissue may have a high stiffness and/or high attenuation. Any limit on the emulation may be provided, such as attempting to prevent a temperature increase of 2 degrees or more Celsius.

In act 32, displacement of the tissue is detected. The excitation causes displacement of the tissue. The displacement may be caused by a longitudinal wave. The displacement may alternatively or additionally be caused by a shear wave.

The displacement is detected with ultrasound scanning. The locations, magnitude, timing, and/or other characteristic of the displacement are detected. For example, locations associated with a threshold amount of displacement caused by the emulation are detected. The locations are at a point, along a line, in an area, or in a volume. For example, the displacement at different locations distributed in three dimensions or over a two-dimensional region is determined.

To detect the displacement, ultrasound energy is transmitted to the tissue undergoing displacement and reflections of the energy are received. The transmission and reception are performed multiple times to determine change due to displacement. Any transmission and reception sequence may be used. The displacement is detected from the differences for each spatial location. For example, the velocity, variance, shift in intensity pattern (e.g., speckle tracking), or other information is detected from the received data as the displacement. The detection of displacement may be interleaved with other scanning, such as scanning different three-dimensional regions for displacement separately and transmitting separate instances of the emulation excitation accordingly.

Any now known or later developed displacement imaging may be used. For example, diagnostic pulses, such as having an intensity and duration below the regulated levels for diagnostic ultrasound, are transmitted. For example, pulses with 1-5 cycle durations are used with an intensity of less than 720 mW/cm$^2$. Pulses with other intensities may be used, such as pulses with less than 1000 mW/cm$^2$. The ultrasound transmission is focused at a region including the tissue to be treated. The transmission may cover one or more scan lines. For example, a wide beam width transmit pulse is used for receiving along two or more receive scan lines with a plane or volume distribution. Alternatively, a single receive beam is formed in response to a transmit. A region may be sequentially scanned. One or more measurements are performed for each receive scan line.

Two or more, such as 2-10, pulses are transmitted to a same location for each measurement or for combining measurements. Alternatively, a single pulse may be transmitted for each measurement. Where the therapeutic intensity and time since cessation are known, a single pulse may be used and compared to pre-emulation or excitation measurement to determine a change in position.

After cessation of the excitation emulating the therapeutic ultrasound, the tissue moves to a relaxed position. Echoes from the multiple relatively low diagnostic imaging pulses are received. The echoes are used to generate one or more images to identify locations with displacement caused by the therapy-associated excitation.

The echoes are detected using B-mode or Doppler detection. Using B-mode data, the data from multiple pulses are correlated. The correlation is one, two or three-dimensional. For example, correlation along a scan line away and toward the transducer is used. Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

The amount of displacement represents regions subjected to force from the excitation associated with HIFU. The time associated with a particular displacement allows estimation of the decay curve. By measuring the displacement as a function of time, the decay of strain from cessation of the excitation may be measured. Displacement alone or any displacement characteristic of the decay may be measured.

In other embodiments, strain or elasticity imaging is used. The displacement of tissue is determined as a function of time. The displacement may be measured from tissue data, such as B-mode ultrasound data. Correlation, cross-correlation, minimum sum of absolute differences or other similarity measure is used to determine the displacement between scans. The displacements are determined along one, two, or three dimensions. In one embodiment, any one or more of the methods or systems disclosed in U.S. Pat. Nos. 5,107,837; 5,293,870; 5,178,147; 6,508,768 or 6,558,324, the disclosures of which are incorporated herein by reference, are used to generate elasticity frames of data or images as the strain information. Other methods of measuring strain may be used. The displacement may be measured by determining tissue velocity and/or acceleration.

Based on one (e.g., velocity), two (B-mode correlation), or more (e.g., average displacement) scans, a strain field is determined. The strain field represents strain at the different locations. A displacement field or a strain rate field may be used in other embodiments. Other measurements may be used to represent strain or displacement, such as velocity.

The displacement is detected over any size region. In one embodiment, the displacement is detected in a region of interest likely to include the tissue to be treated, such as about ⅓ to ½ the complete scan region for B-mode imaging. FIG. 3 shows one embodiment where the image on the left shows a region of interest box for displacement imaging. Greater, lesser, or no region of interest may be used, such as detecting displacement over the entire imaging region. Narrower regions of interest may allow for displacement detection with fewer repetitions of transmitting the excitation waveform associated with HIFU. Depending on the number of receive beams that may be formed and the sample density, none, one, or more repetitions may be used. Full sampling, such as sampling displacement on every B-mode sample location, may be used. Greater or lesser (e.g., sparse) sampling of displacement relative to the B-mode scan grid may be used.

In one embodiment, shear waves are detected in addition to or as an alternative to longitudinal waves. The excitation forms a beam, which generates a shear wave at spatial locations. Where the beam is sufficiently strong, a shear wave is generated. The shear wave propagates through tissue more slowly than the longitudinal wave along the acoustic wave emission direction. The shear wave propagates various directions, including a direction perpendicular to the direction of the applied stress. The displacement of the shear waves is greater at locations corresponding to the excitation beam.

Ultrasound data is obtained. At least some of the ultrasound data are responsive to a shear wave. A region of interest is monitored to detect the shear wave. The region of interest is any size, such as 6 mm in lateral and 10 mm in axial. This detection region is monitored by ultrasound. For example, B-mode scans are performed to detect tissue displacement caused by the shear wave. Doppler, color flow, or other ultrasound mode may be used to monitor for the shear wave.

The monitoring is performed for any number of scan lines. For example, four receive beams are formed in response to each transmission. After transmitting the excitation to generate the shear wave, B-mode transmissions are performed repetitively along a single scan line and receptions along four adjacent scan lines. Any number of repetitions may be used, such as about 120 times. Some of the ultrasound data, such as at the beginning or end of the repetitions, may not be responsive to the shear wave. In other embodiments, only a single receive beam or other numbers of receive beams are formed in response to each transmission.

As the shear wave propagates through the scan lines, the B-mode intensity may vary. For the monitored scan lines, a sequence of data is provided representing a time profile of tissue motion resulting from the shear wave. For example, data from a plurality of spatial locations (e.g., along the scan lines) is correlated as a function of time. Any elasticity detection may be used. For each depth or spatial location, a correlation over a plurality of depths or spatial locations (e.g., kernel of 64 depths with the center depth being the point for which the profile is calculated) is performed. Two or three-dimensional displacement in space may be used. One-dimensional displacement along a direction different than the scan lines or beams may be used.

The spatial offset with the highest or sufficient correlation at a given time indicates the amount of displacement. Displacements are determined for a given location at different times. The temporal profile for a given location indicates detection of the shear wave. The profile is examined for a non-noise or single instance of variation. A peak in the profile, with or without temporal low pass filtering, indicates the passing of the shear wave front. The greatest displacement is selected, but the average or other displacement statistic may be used. The maximum shear at a given location is detected. Alternatively, an average or other shear is detected.

To monitor a larger region, additional receive beams are formed in response to the monitoring transmit beam. Alternatively, another shear wave is generated and the transmit beams and receive beams are provided at a different distance from the shear wave generation point. In the 6 mm×10 mm example above, 36 receive scan lines may be provided. At four receive beams per transmit beam, the process is repeated for different lateral spacing nine times. For each receive beam location, a time profile of motion information is provided, represented by the ultrasound data. Transmissions along different scan lines to monitor a same shear wave are avoided during formation of the temporal profile to provide higher temporal resolution, but interleaved or shifting scanning positions may be provided.

The discussion above is for one depth. The sampling may be arranged to provide one gate covering the entire axial extent of the region of interest. In another embodiment, samples are obtained at multiple depths for each receive beam. A separate time profile is provided for each axial depth as well as lateral location. Any number of depths may be used, such as about 200 for 5 mm or 400 for 10 mm.

Ultrasound data representing different locations in the region of interest is obtained. The ultrasound data are obtained in real-time with the scanning or obtained from a memory. For each location, the motion information represents the response at different times. Other scanning, monitoring, or techniques may be used to obtain ultrasound data to estimate shear magnitude.

The tissue may change over time, such as where the detection of the shear wave is interleaved with actual application of the therapy HIFU. The stiffness of the tissue may increase in the treatment locations. This change in stiffness may alter the detected magnitude of the shear. Shear velocity and/or modulus or other complex representation of shear may be used to minimize or avoid the effects of changes in the tissue. Shear velocity may be preferred where the modulus is otherwise not available or difficult to determine. The absorption coefficient may be assumed (e.g., 0.5, 0.6, 0.8 or other value) depending on the tissue being treated. The shear velocity and/or modulus may be determined, at least in part, based on the pressure and absorption coefficient. The pressure applied is known from the transmitted excitation and consideration of attenuation.

Shear velocity is detected for the different spatial locations of the tissue. For each location, the displacement as a function of time is determined. The shear velocity is obtained by determining a time from generation of the shear wave until detection of the shear wave at a different location. The time and distance to the location determine the velocity. The distance is known from the scan line spacing (i.e., the transmit beam position for generating the shear wave and the receive beam position for detecting the shear wave). The time is known from the relative time between generation and detection of the shear wave.

Other techniques may be used to detect the peak in the profile. For example, a regression is applied. Since the shear wave velocity is linear, a robust linear regression with automated outlier detection may indicate the shear wave velocity. The ultrasound data for all of the sample points in the region of interest is plotted for distance as a function of time or by time and distance. The linear regression is applied to the plot or data, providing a line fit to the data. The slope of the line indicates the shear wave velocity.

Other approaches may be used. For example, data from different times is correlated to detect the shift in tissue caused by the shear wave. As another example, a feature is extracted from the temporal profiles. Principal component decomposition may be used. A correlation between the different temporal profiles is performed. The lag associated with the different distances for the different temporal profiles provides the velocity. Alternatively, a wavelet analysis may be performed. A wavelet transform is applied to the temporal profiles to identify a peak corresponding to the shear wave. A velocity value is identified from the travel time of the peak to each spatial location.

All the peak travel time data from the full region of interest may be used together, such as in linear regression. Only a subset of the data may be used, such as using data for one depth for feature extraction or regression. Shear velocities may be calculated for each location in the region of interest. Alternatively, a spatial representation of shear wave velocity variance within the region of interest may be provided.

In approaches by others, any modulus or shear value may be estimated. Tissue modulus values represent the hardness or stiffness at the locations. For example, the shear modulus of tissue is estimated. In alternative embodiments, Young's modulus is estimated. In other embodiments, other shear values are estimated, whether quantitative or qualitative.

The shear modulus is given by $g=\rho v_s^2$, where $\rho$ is density, and $v_s$ is estimated shear velocity. In one embodiment, the tissue moduli or shear information, such as the shear modulus, is determined as a function of the strain or displacement and the moduli or shear information. For example, the shear modulus for each sample location is determined by iteratively solving a diffusion equation. Assuming a Poisson's ratio of 0.5 or using a known Poisson's ratio, the shear modulus at different locations is calculated iteratively as a function of the strain field at different times or under different stress for the different locations and the shear modulus.

In act 34, a beam location for the HIFU is determined using the displacement of tissue information. Locations associated with sufficient magnitude of displacement, strain, strain rate, shear, shear velocity, or shear modulus are identified. Where examples or embodiments use displacements, alternatively strain, strain rate, shear, shear velocity, or other derivatives of displacement may be used. Locations where the displacement is relatively high are identified by applying a threshold. The threshold may be preprogrammed or adapted to a given data set. The threshold may be normalized, such as a threshold based on data at spatial locations spaced away from the likely location of the beam. As another example, an average or other percentage displacement across a region of interest is determined. Locations associated with a maximum displacement greater than the average or other percentage indicate beam locations. In other or additional embodiments, no threshold is applied, or a noise threshold is used. The range of displacements are mapped to display values such that low or no displacement regions are at one end of the dynamic range and the highest displacements are at the other end of the dynamic range. Linear or non-linear mapping may be used.

The displacement data may or may not be spatially filtered prior to application of the threshold. The displacements may be low pass filtered after application of the threshold.

In act 35, the displacement data is used to calculate a line, a point, other shape, or combinations thereof. Any shape may be used, such as the line, the point, elongated ellipses, rectangles, stylized triangles, arrows, arrow-heads, or curves. The shape may be fit to intensity patterns to capture the focal and/or near field shape of the beams. The response of the tissue to the excitation is used to determine the scan line, focal point, or other sub-region of the displacements. The distribution of the displacements indicates the center line, focal point, or any representative shape as affected by any aberrations, tissue differences, or other deviations from ideal. Multiple points or different lines may be calculated. In examples herein, point and line are used. Other shapes may alternatively be used.

The line or point is determined within an area or a volume. For example, the location of the line or point is determined using displacements representing a volume. The location of the point may be determined in a one dimensional region, such as the location being along a line. Displacement is measured for just the line or area, but may be measured for regions with additional dimensions even if not used to determine the location of the line or point.

The displacement data may be segmented prior to determining the line or point location. A region of sufficient displacement may have different shapes, such as associated with bifurcation of an organ or intervention of bone or other structure. More than one separate region of contiguous locations of displacement may result from the displacement measurement. The segmentation selects the most likely or desired region for fitting to the line or point.

Figure 4:
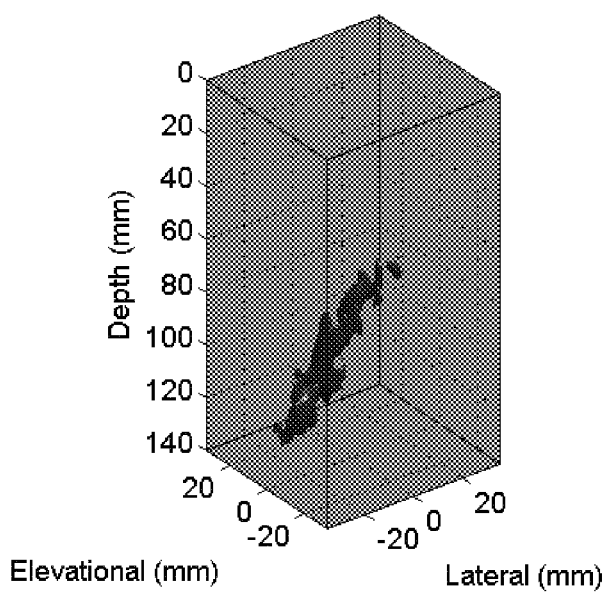
FIG. 4 is a three-dimensional rendering of a segmented strain region in one example.

FIG. 4 shows a three-dimensional rendering of a segmented strain region in one example. The volume corresponding to the regions of greatest strain within the field of view are automatically segmented. The segmented region is used to determine a center line and focus of the targeting beam, thereby providing feedback between the intended and actual focus of therapy. The graph coordinates of FIG. 4 are the imaging probe coordinate, but could be display coordinates. Separate HIFU transmitter and imaging transducer probes are used, offset from each other. The HIFU transmitter is on the top right with a 45° angle facing down to the lowerleft. The imaging transducer probe is at a top of the box, generally centered. A common probe and/or other relative arrangements may be used.

Any segmentation technique may be used. In one embodiment, an adaptive threshold is used with volume or area growth. For example, the threshold is set to include about only 5% of the displacements (or related measurements such as strain). After the threshold is determined from the displacement field, the threshold is applied to the displacement locations. A location is tested for having displacement above the threshold. If above, the region is grown by testing the displacement of adjacent locations against the threshold until the region cannot be grown more. Then, untested locations are examined and grown if above the threshold. The result is likely a plurality of different grouped locations having higher displacement than the rest. The largest contiguous region or region associated with the greatest number of adjacent or connected locations also above the threshold is selected. Other region growing, thresholds, or segmentations may be used.

For the selected region, the locations for the region are used to calculate a line or point. The selected region may be expanded further to include the displacements below the 5% or other threshold. The selected region may be filtered to fill any gaps.

The line is calculated from the coordinates of the locations within the region. A region shrinking may be used, such as a skeleton operation. In one embodiment, a regression analysis is performed to fit a straight, curved or other line to the region. The line is through the center or other location of the region, indicating the location of the center of the HIFU or emulation beam. The center line, such as a center straight line, indicates the center of the response of the excitation and corresponding displacements. Lines may be fit to other regions.

The point may be calculated independently of the line. For example, a maximum displacement (e.g., strain) in the displacement field is determined. The point may be determined with or without segmentation. The point may be a center of gravity for a region, such as the largest segmented region. In one embodiment, the point is a maximum displacement value (e.g., highest echo strain value) along a line, such as the line determined as a center line. The displacements along the line may be low pass filtered in addition to any other filtering before determining the location of the maximum or center.

More than one point may be determined. For example, all the points along a line, in an area or in a volume above a set or adaptive threshold are identified. As another example, a certain number of points above a threshold up to a maximum number are identified (e.g., the highest three values above a threshold). These additional points may represent regions of likely cavitation or bubble generation as indicated by the displacement information.

Figure 5:
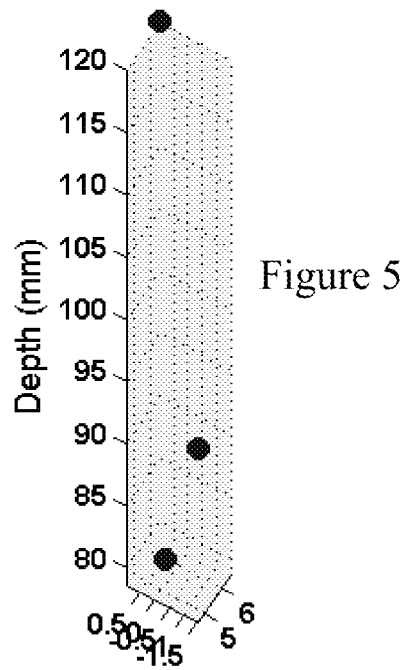
FIG. 5 is an example grid display of detected points relative to a transducer.

FIG. 5 shows an example grid display of detected points relative to a transducer. The points are from different transmitted emulations with different focal depths. The grid display indicates the location relative to the HIFU transmitter, but may be relative to any separate imaging probe. As an alternative to a grid display, one or more points may be displayed with a B-mode image (see left side of FIG. 3), a displacement image (see right side of FIG. 3 or FIG. 4), or combinations thereof.

The locations are used without the magnitude of the displacements for determining the line or point. In other embodiments, the line or point determination is weighted as a function of the displacements for the locations.

Figure 6:
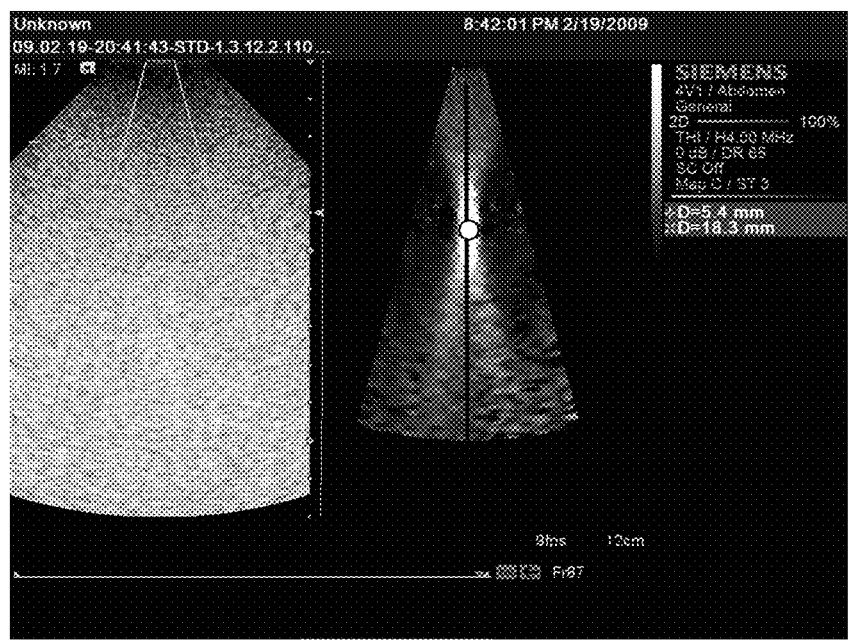
FIG. 6 is one embodiment of the image of FIG. 3 with the center line and a point overlaid thereon.

In act 36, image data is generated. The image data includes image values indicating the line, the point or both the line and the point. FIG. 5 shows one example. The line and/or the point are graphic overlays of an image, such as B-mode or displacement image (see FIG. 3). For example, FIG. 6 shows the displacement image of FIG. 3 with a center line and focal point highlighted with a graphic overlay. The graphic overlay is in black and white, grayscale or color. The line may be thick, thin, solid, dashed or other format. The point may be displayed as a point, a circle, cross-hairs, or other indicator. Alternatively, the line and/or point are shown by different mapping of brightness, color, hue or other display characteristic than surrounding pixel or voxels. For example, the displacement values are gray scale or color mapped. The line and/or point are similarly gray scaled or color mapped, but with different intensity, color, or brightness. In one embodiment, the line is displayed with a dot graphic to indicate the point along the line. By mapping or overlaying in a B-mode or displacement image, the line and/or point are shown relative to tissue. The line and/or point may be shown without or with other image information and/or displacement information.

More than one line or point may be shown in the image. For example, a plurality of points is indicated. The points represent locations of likely bubble generation, cavitation or other effects that may influence treatment decisions.

The displacements or B-mode data for a two-dimensional region are scan converted into a display format. The line or point is positioned in the scan converted region. Alternatively, the displacements or B-mode data for a three-dimensional region are rendered to a two-dimensional image using surface rendering, ray casting, or other volume rendering. The line and point are positioned in the volume prior to rendering or on the rendered image as seen from the viewer's perspective. The images may be only of the line or point from the viewer's perspective.

In one embodiment, the image is a multidimensional image showing a spatial extent and location of a beam profile of the excitation within the tissue. The displacements or measurements derived from displacements (e.g., strain or shear) are shown in the image. This information represents the beam profile. The line, point, or line and point are graphically overlaid on or combined with this beam profile.

The beam profile is shown as function of the displacement. For example, the image represents the beam profile of the excitation. The beam profile corresponds to locations with sufficient displacement. The image shows the location of the beam, including the spatial distribution of the beam. The image represents the spatial extent of the beam profile in one or more dimensions. FIG. 3 shows an image on the right side of the beam. Brighter or more intense locations correspond to greater displacement. The image may be filtered, such as low pass filtered.

The displacement data is in a display format or may be scan converted into a display format. The displacement data is color or gray scale data, but may be data prior to mapping with gray scale or color scale. The information may be mapped linearly or non-linearly to the display values.

The image represents the displacement information, such as shear or moduli (e.g., the shear moduli) for the different locations. Where the values are determined for all of the grid points in a region of interest or field of view, the pixels of the display represent the beam for that region. The display grid may be different from the scan grid and/or grid for which displacements are calculated. Color, brightness, luminance, hue, or other characteristic is modulated as a function of the displacement.

The image may include other data, such as the line or point information. For example, B-mode or other data representing tissue, fluid, or contrast agents in the same region is included.

The displacement data is used for an overlay of or combination with the other data. The other data assists the user in determining the location of the beam relative to the tissue to be treated.

In an alternative embodiment, the image is generated as a function of the displacement and a beam profile model. The displacement may be noisy. A model of the therapy beam is provided. The model may be generated using empirical information or theoretical calculation. The beam profile model is created as an inverse problem to determine the likely distribution of the beam profile. The spatial and temporal displacement may be formulated based on the beam profile model. Given the measured displacements and models, a representation of the best fit or least square fit of the measurements to the model is determined. The fit representation is used for generating the image, such as a graphic overlay sized and shaped based on the fit. The beam profile represented by the image is reconstructed by fitting a model to the measured displacements. The model may include a center line and/or focal point. The fitting of the model may also include fitting the center line and/or point, such as through an elastic function or least squares fit.

In act 38, the beam profile is corrected as a function of acoustic propagation. The measured displacement is or is not corrected for depth dependent attenuation of the applied stress. As pressure propagates through tissue, the pressure attenuates. Less motion or displacement is caused at locations spaced further from the source of pressure (depth relative to the source) due to the attenuation. The displacement is adjusted to account for the attenuation, providing more normalized displacements or strain at different depths.

The correction is linear as a function of distance away from the point or region of the source (e.g., transducer) of stress. Non-linear correction may be used, such as based on tissue models or different types of tissue. The linear or non-linear function is assumed, based on empirical data, or is based on a propagation model. For acoustic force, the attenuation of sound in tissue as a function of distance and frequency is corrected. In other embodiments, no correction for attenuation and/or frequency is performed.

In act 40, high intensity focused ultrasound therapy waveforms are transmitted. High voltage waveforms are applied to the high intensity focused ultrasound transducer, which generates the HIFU therapy waveforms in the acoustic domain. The HIFU pulse is focused using a phased array and/or mechanical focus and provides the high intensity acoustic energy to tissue at a focal or beam location. The therapeutic ultrasound pulse has a plurality of cycles at any desired frequency. In one embodiment, the therapeutic pulse lasts for a fraction of a second to seconds at an ultrasound frequency, such as 500 KHz-20 MHz. Any peak intensity may be provided, such as 100 or more watts per square centimeter, 500 or more watts per square centimeter, 1000-2000 watts per square centimeter, or about 1000 watts per square centimeter. Any now known or later developed therapeutic waveform with any intensity, frequency, and/or number of cycles may be used. The waveform is continuous or intermittent.

The therapeutic ultrasound pulse treats the tissue by generating heat at the desired tissue location. The intensity also generates stress on the tissue. The pulse pushes the tissue towards and away from the transducer with negative and positive acoustic pressures. For a sufficiently long therapeutic pulse, a substantially constant strain on the tissue is created. The strain, $\epsilon$, is a function of the tissue stiffness, E, the viscosity, $\eta$, and the stress from HIFU radiation force. The steady state stress during the therapeutic pulse is proportional to the ratio of average HIFU intensity, I, to the speed of sound in the tissue, c.

The HIFU waveforms also generate biomechanical changes that can be detected. The thermal effects of the therapy acoustic energy may cause changes in volume due to thermal expansion, in the speed of sound (c), in tissue stiffness (E), and/or in the viscosity ($\eta$) of fluids in the tissue. The therapy acoustic energy may also induce mechanical effects, such as radiation pressure, streaming, and/or cavitations. The biological effects may include hyperthermia at tissue temperature of about 41-45° C., protein denaturation at temperatures above 45° C., and tissue necrosis at temperatures above 50° C. Tissue stiffness may be affected even at temperatures below 45° C. At temperatures above 45° C., increases in viscosity and/or stiffness may occur. At temperatures above 50° C., the tissue may have a high stiffness and/or high attenuation.

Before subjecting the tissue to treatment, the position of the HIFU beam is determined from the image generated in act 36. The user may reposition the transducer, a focal location, or change other settings to position the beam over the tissue to be treated while minimizing healthy tissue subjected to the HIFU. Automated positioning may be used in other embodiments, such as where the tissue to be treated is determined using computer assisted diagnosis. The power level may be changed as well. The power level is changed based on the beam profile, center line, or point(s) of higher intensity. After positioning the beam as desired, the HIFU is transmitted in act 40.

The HIFU may be continuous or sporadic. Any treatment regimen may be used. During ongoing treatment or in between different fractions of the treatment, the imaging of act 36 may be performed. The therapy waveforms of act 40 are interleaved with the imaging of act 36. The imaging of act 36 is performed using the transmitting of act 30, the detection of act 32, the determination of act 34, and the calculation of act 35. The HIFU treatment ceases while the beam location is determined. Alternatively, the HIFU transmissions of act 40 are used as the excitation for detecting displacement in act 32. The HIFU may cease for detection of displacement, or the displacement due to the HIFU waveforms is used. In another alternative, the HIFU is performed at one frequency or coding, and the transmission of the excitements and corresponding reception are performed at a different frequency or coding, allowing operation at the same time given pre-treatment tissue position information. The interleaving allows user or system positioning of the HIFU beam on an on-going basis. If the patient or transducer shifts position, the beam may be altered to treat the appropriate tissue. If the speed of sound in the tissue changes due to the treatment, the beam may be altered to treat the appropriate tissue.

In act 44, a change in the tissue from high intensity focused ultrasound therapy is determined. For example, the change in the displacements is determined. HIFU may cause the tissue to be less elastic or stiffer. Ablation, collagen denaturization, coagulation, or other effects may alter the shear velocity or other characteristic. The amount of displacement given a same or known but different stress may be determined. The amount or magnitude of displacement may be measured. Any measurement may be used, such as a median or mean of change in displacement for a region. Changes in shear, strain, elasticity, modulus, velocity, or other tissue characteristic may be measured. The changes in tissue may result in different center line locations, different point locations, and/or additional points. The highlighting of the line and/or points in the image may assist the user in viewing the effects of ongoing treatment in order to alter future treatment.

The change is determined by the user or by the system. For example, a quantity is determined. As another example, the user detects the change based on one or more images, such as identifying additional points associated with high intensity before or after the focal position or such as identifying a shift in the center line. The change may be detected automatically, such as quantifying an amount of change, a direction of change, an increase in number of points, or other measure of the change.

The change may be used for feedback control of dosing. In act 42, the application of HIFU in act 40 may be altered or ceased based on the change. The dosage of the high intensity focused ultrasound therapy is altered as a function of the change. To minimize damage to healthy tissue, the HIFU intensity or duration may be reduced where sufficient treatment has occurred. The change in tissue indicates sufficiency of treatment. To avoid ineffective treatment, the HIFU intensity or duration may be increased where insufficient treatment has occurred, as reflected by less than expected change. The focal position and/or steering angle used for HIFU may be changed based on the center line and/or point information. The change may position the center line at a more desirable location. The change may reduce or increase locations likely to be associated with cavitation or bubble generation.

FIG. 2 shows one embodiment of a system 10 for providing feedback for high intensity focused ultrasound. The system 10 implements the method of FIG. 1 or other methods. The system 10 includes a transmit beamformer 12, a transducer 14, a receive beamformer 16, an image processor 18, a display 20, a memory 22, and a HIFU transducer 24. Additional, different or fewer components may be provided. For example, a user input is provided for manual or assisted alteration of a beam profile (e.g., selection of frequency, focal depth, scan line angle, aperture, focal location, and/or apodization). As another example, the transducer 14 and the HIFU transducer 24 are a same transducer. The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed. A sequence of transmit beams are generated to scan a two or three-dimensional region. Sector, Vector®, linear, or other scan formats may be used. The same region is scanned multiple times. For flow or Doppler imaging and for strain imaging, a sequence of scans is used. In Doppler imaging, the sequence may include multiple beams along a same scan line before scanning an adjacent scan line. For strain imaging, scan or frame interleaving may be used (i.e., scan the entire region before scanning again). In alternative embodiments, the transmit beamformer 12 generates a plane wave or diverging wave for more rapid scanning.

The same transmit beamformer 12 is shown for generating HIFU and/or emulation waveforms with the HIFU transducer 24 and displacement detection with the imaging transducer 14. In alternative embodiments, different transmit beamformers 12 are provided for imaging displacement and therapy. For example, a separate therapy system is used. The transducer 14 and transmit beamformer 12 are used to image displacement for operating the separate therapy system. In another alternative, the same transducer 14 is used for both detecting displacement and applying therapy. One or more elements are used for both therapy and diagnostic transmissions.

The high intensity focused ultrasound transducer 24 generates high intensity focused ultrasound therapy waveforms. The HIFU transducer 24 is an array for generating acoustic energy from electrical waveforms. One or multidimensional arrays may be used. Alternatively, a single element with a mechanical focus is used. For an array, relative delays focus the acoustic energy. A given transmit event corresponds to transmission of acoustic energy by different elements at a substantially same time given the delays. The transmit event provides a pulse of ultrasound energy for treating the tissue. Alternatively, a mechanical focus is provided for the array. Any now known or later developed therapy transducer 24 may be used.

In one embodiment, the HIFU transducer 24 is separate from the imaging transducer 14. The imaging transducer 14 is moveable separate from the HIFU transducer 24. Imaging is used to determine the therapy location. The imaging transducer 14 receives echo signals responsive to one or more transmissions from the HIFU transducer 24. For example, signals responsive to an emulation of therapy waveforms are received. Alternatively or additionally, both transducers 14, 24 include spatial registration systems, such as magnetic position sensors. The transducers 14, 24 are not connected together, but may be, such as being positioned in a same housing.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a two-dimensional PZT array (e.g., about 3,000 elements). Receive signals are generated in response to ultrasound energy (echoes) impinging on the elements of the transducer 14. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for displacement. Alternatively, the B-mode data is also used to determine displacement. The beam summed data may be responsive to transmission of an emulation of the HIFU waveforms. By transmitting the emulation, the tissue is displaced. The displacement may be measured using ultrasound.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples.

In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement, and calculating tissue properties. For example, the separate processor performs any combination of one or more of the acts shown in FIG. 1.

The processor 18 estimates tissue displacement as a function of beamformed samples. The displacement is due to transmission of an emulation of HIFU or the actual HIFU operation. Any type of displacement may be estimated. For example, the processor 18 detects shear wave displacement information. In another example, the processor 18 applies modulus, or shear velocity estimation. The processor 18 determines information as a function of the output data from the receive beamformer 16.

The processor 18 determines a sub-region associated with the displacement information (e.g., strain, shear, or actual displacement). The sub-region may be a volume, area, line, or point. In one embodiment, a center line of the beam profile is determined. The beam profile is represented by a contiguous region of tissue displacement, such as two or three-dimensional region determined by segmentation. In another embodiment, one or more points associated with greater displacement within the beam profile region are determined.

The processor 18 outputs image or display values mapped from the tissue properties to the display 20. For example, the maximum displacement, shear velocity, shear modulus, or other value is determined for each location. The magnitude of the values modulates the color, hue, brightness, and/or other display characteristic. An image of the beam profile represented as tissue displacement in generated from the modulated display values. The image may be shown alone or overlaid or combined with other images (e.g., B-mode image).

FIG. 3 shows an image of a beam profile. The brighter regions correspond to greater displacement. The displacement values are based on displacement due to an emulation of the HIFU therapy waveforms or the therapy waveforms themselves. The emulation or actual therapy waveforms are transmitted from the HIFU transducer 24 so that the beam position corresponds to the treatment beam. The image represents a spatial extent of the beam profile and/or relative position in a patient.

The imaging may include the sub-region. The sub-region is shown relative to the displacement region or to tissue. For example, different mapping of the displacement information along the sub-region (e.g., line or point) is provided than for other displacements. As another example, a graphic representing the location of the sub-region is overlaid on the image.

In one embodiment, the processor 18 is a control processor. The processor 18 controls use of the HIFU therapy waveforms. Based on detected changes in the tissue displacement and/or the location or changes in the location of the center line, point, or other sub-region of the displacements, the processor 18 determines whether to cease the therapy prior to a scheduled end.

For determining displacement, data from a plurality of scans or measurements may be acquired and stored. The data is stored in the memory 22 or a different memory. Data from one or more stages of processing is stored, such as radio frequency data, channel data, beam sum data, detected data, strain data, shear data, modulus data, shear modulus data, and/or calculated values.

The processor 18 operates pursuant to instructions stored in the memory 22 or another memory. The processor 18 is programmed for providing feedback for high intensity focused ultrasound. The memory 22 is a computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 displays one or more images representing the HIFU beam profile. The spatial distribution of displacement associated with HIFU is shown in the image. The image represents the spatial extent of the beam profile and relative position of the patient. The image may additionally or alternatively represent a line, point, points, or other sub-region of the beam profile.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. In a non-transitory computer readable storage medium having stored therein data representing instructions executable by a programmed processor for providing feedback for high intensity focused ultrasound, the storage medium comprising instructions for:

transmitting an emulation of a high intensity focused ultrasound therapy waveform, the emulation having a different amplitude, duration, or both amplitude and duration from the therapy waveform, the emulation substantially avoiding therapy heating and cavitation;

determining displacements at a plurality of locations in a multi-dimensional region with ultrasound scanning, the locations of displacements being caused by the emulation;
computing a shape of the displacements; and
generating an image highlighting the shape.

2. The computer readable storage medium of claim 1 wherein computing the shape comprises computing a center line;
further comprising:
computing a maximum point of the displacements along the center line.

3. The computer readable storage medium of claim 1 further comprising instructions for determining a change in the tissue from high intensity focused ultrasound therapy as a function of the displacements, and altering dosage of the high intensity focused ultrasound therapy as a function of the change.

4. A method for providing feedback for high intensity focused ultrasound, the method comprising:
transmitting an excitation from a high intensity focused ultrasound transducer into tissue of a patient;
detecting displacements of the tissue caused by the excitation;
calculating shape for a response of the tissue to the excitation as a function of the displacements of the tissue; and
generating an image indicating the shape relative to the tissue.

5. The method of claim 4 wherein calculating the shape comprises calculating a center line the response to the excitation.

6. The method of claim 5 wherein calculating the center line comprises fitting a straight line to a largest contiguous region of the displacements.

7. The method of claim 6 wherein calculating the shape comprises calculating a point as a maximum value along the center line.

8. The method of claim 4 wherein calculating the shape comprises calculating a point as a function of the displacements.

9. The method of claim 8 further comprising:
calculating an additional point as a function of the displacements;
wherein generating the image comprises generating the image indicating the point and the additional point.

10. The method of claim 4 wherein detecting displacement comprises detecting displacements in three-dimensions, and wherein calculating the shape comprises calculating a line, a point, or the line and the point from the displacements distributed in the three-dimensions.

11. The method of claim 4 further comprising:
transmitting high intensity focused ultrasound therapy waveforms with the high intensity focused ultrasound transducer;
interleaving the therapy waveforms with repetitions of the transmitting the excitation and detecting; and
correcting the transmitting of the high intensity focused ultrasound therapy waveforms as a function of the shape.

12. The method of claim 4 wherein transmitting the excitation comprises transmitting the excitation as an emulation of a high intensity focused ultrasound therapy waveform, the emulation having a different amplitude, duration, or both amplitude and duration from the therapy waveform, the emulation substantially avoiding therapy heating and cavitation, and the therapy waveform provides heating or cavitation.

13. The method of claim 4 wherein detecting displacement of the tissue comprises detecting shear waves caused by the excitation.

14. The method of claim 4 wherein detecting displacement comprises detecting strain.

15. The method of claim 4 wherein generating the image comprises generating the image with a multidimensional image showing a spatial extent and location of a beam profile of the excitation within the tissue where the shape is graphically overlaid on the beam profile.

16. The method of claim 4 further comprising:
determining a change in the tissue from high intensity focused ultrasound therapy as a function of the displacements; and
altering dosage of the high intensity focused ultrasound therapy as a function of the change.

17. A system for providing feedback for high intensity focused ultrasound, the system comprising:
a receive beamformer operable to output data representing spatial locations as a function of received acoustic signals;
a processor operable to estimate tissue displacements as a function of the output data, determine a sub-region of a region of contiguous tissue displacements, and generate an image with the sub-region highlighted; and
a display operable to display the image of the sub-region.

18. The system of claim 17 wherein the sub-region comprises a line determined by the processor from the region of contiguous tissue displacements, the region being a two or three-dimensional region.

19. The system of claim 17 wherein the sub-region comprises a point determined by the processor from the region of contiguous tissue displacements, the region being a two or three-dimensional region.

20. The system of claim 17 wherein the data is responsive to a transmission, the transmission comprising an emulation of the high intensity focused ultrasound therapy waveforms, wherein the tissue displacement comprises a shear wave displacement, wherein the tissue displacement represents a beam profile of the emulation, and wherein the image represents a spatial extent of the beam profile and relative position in a patient.

21. The system of claim 17 wherein the processor is operable to control use of high intensity focused ultrasound therapy waveforms, the use controlled as a function of the sub-region.

* * * * *